United States Patent [19]

Märky

[11] 4,231,957
[45] Nov. 4, 1980

[54] PHOSPHONIUM COMPOUNDS, A PROCESS FOR THEIR PREPARATION AND A PROCESS FOR THE PREPARATION OF ASYMMETRICALLY SUBSTITUTED STILBENE FLUORESCENT BRIGHTENING AGENTS

[75] Inventor: Michael Märky, Binningen, Switzerland

[73] Assignee: Ciba-Geigy Corporation, Ardsley, N.Y.

[21] Appl. No.: 950,902

[22] Filed: Oct. 12, 1978

[30] Foreign Application Priority Data

Nov. 4, 1977 [LU] Luxembourg ............................ 78449

[51] Int. Cl.$^3$ ....................... C07C 143/24; D06P 1/38
[52] U.S. Cl. .................................................. 260/505 C
[58] Field of Search .................................... 260/505 C

[56] References Cited

U.S. PATENT DOCUMENTS 3,984,399   10/1976   Weber et al. ...................... 260/505 C

*Primary Examiner*—Alan Siegel
*Attorney, Agent, or Firm*—Prabodh I. Almaula

[57] ABSTRACT

Phosphonium compounds of the formula

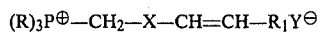

in which R is preferably alkyl having 1 to 4 C atoms, cyclohexyl or phenyl, $R_1$ is a substituted or unsubstituted aromatic radical, especially a phenyl radical, X is phenylene, 4,4'-biphenylene or 1,4- or 2,6-naphthylene and $Y^\ominus$ is $SO_3^\ominus$, $SO_2^\ominus$ or $COO^\ominus$, a process for their preparation and a process for the preparation of asymetrically substituted fluorescent brightening agents of the formula

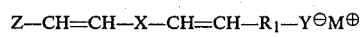

in which $R_1$, X and $Y^\ominus$ are as defined above, $M^\oplus$ is a cation and Z is preferably a substituted or unsubstituted phenyl or 2-phenyl-triazol-4-yl radical, by reacting a bis-phosphonium compound of the formula

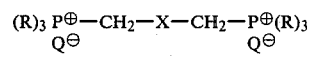

in which $Q^\ominus$ is an anion, with an aldehyde of the formula $M^\oplus Y^\ominus$—$R_1$—CHO and reacting the resulting intermediate with an aldehyde of the formula Z—CHO.

6 Claims, No Drawings

PHOSPHONIUM COMPOUNDS, A PROCESS FOR THEIR PREPARATION AND A PROCESS FOR THE PREPARATION OF ASYMMETRICALLY SUBSTITUTED STILBENE FLUORESCENT BRIGHTENING AGENTS

The present invention relates to novel phosphonium compounds, a process for their preparation and a process for the preparation of asymmetrically substituted stilbene fluorescent brightening agents.

The novel phosphonium compounds have the formula

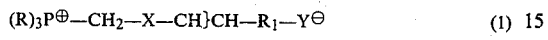  (1)

in which R is alkyl having 1 to 6 C atoms, cycloalkyl having 5 to 7 C atoms, aryl or the group $-NX_1X_2$, in which $X_1$ and $X_2$ independently of one another are alkyl having 1 to 4 C atoms or together with the N atom are a 5-membered or 6-membered saturated heterocyclic ring, $R_1$ is a mononuclear or binuclear aromatic carbocyclic or heterocyclic radical, which can contain further non-chromophoric substituents, X is phenylene, 4,4'-biphenylene or 1,4- or 2,6-naphthylene and $Y^\ominus$ is $SO_3^\ominus$, $SO_2^\ominus$ or $COO^\ominus$.

Preferred alkyl radicals R are those having 1 to 4 C atoms, especially the isopropyl radical and the n-butyl radical.

The preferred cycloalkyl radical is the cyclohexyl radical.

Aryl radicals R can be unsubstituted or substituted by alkyl having 1 to 6, preferably 1 to 4, C atoms, alkoxy having 1 to 6, preferably 1 to 4, C atoms, chlorine, fluorine, bromine, iodine, cycloalkyl having 5 to 7 ring members, phenyl, mononuclear or binuclear phenoxy or the group $-NX_1X_2$, in which $X_1$ and $X_2$ are as defined under R. The aryl radicals R are preferably mononuclear. The phenyl radical is preferred. 5-membered or 6-membered saturated heterocyclic rings $-NX_1X_2$ are preferably the pyrrolidine, morpholine and piperidine radical.

The compounds of the formula (1) are in the form of inert salts.

Aromatic radicals $R_1$ are preferably the phenyl radical and the α- or β-naphthyl radical and heteroaromatic radicals $R_1$ are the furane, thiophene, oxazole, isoxazole, pyrazole, imidazole, 1,2,3-triazole, 1,2,4-triazole, 1,2,3-oxadiazole and 1,3,4-oxadiazole radical. These radicals can also contain a fused benzo or naphtho radical which is unsubstituted or substituted by non-chromophoric substituents.

Non-chromophoric substituents of the radicals $R_1$ are, in addition to the obligatory substituent $Y^\ominus$, the following: chlorine, bromine, fluorine, $C_1$–$C_8$ alkyl, $C_3$–$C_7$ alkenyl, $C_5$–$C_7$ cycloalkyl, $C_1$–$C_8$ alkoxy, $C_2$–$C_{12}$ alkoxyalkoxy, phenoxy, phenyl, cyano, carboxyl, carbalkoxy and sulpho. Preferred substituents are in general $C_1$–$C_4$ alkyl or alkoxy, $C_3$ or $C_4$ alkenyl, fluorine, chlorine, bromine, $C_2$–$C_5$ carbalkoxy and sulpho. If $R_1$ carries further substituents in addition to $Y^\ominus$, these are preferably 1 or 2 substituents.

"Sulpho" and "carboxyl" are to be understood as meaning the groups $-SO_3H$ and $-COOH$ respectively and also the salts thereof, especially the alkali metal salts, alkaline earth metal salts, ammonium salts or amine salts thereof.

The group $Y^\ominus$ is preferably the $SO_3^\ominus$ or $COO^\ominus$ group, especially the $SO_3^\ominus$ group.

Amongst the compounds of the formula (1), preferred compounds are those of the formula

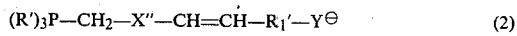  (2)

in which $R_1'$ is a phenyl, naphthyl, furan, thiophene, oxazole, isoxazole, pyrazole, imidazole, triazole or oxadiazole radical which in addition to the group $Y^\ominus$ can carry one or two further non-chromophoric substituents, it being possible for two adjacent substituents also to form the member necessary to complete a fused benzo or naphtho radical, R' is alkyl having 1 to 4 C atoms, cyclohexyl or phenyl, $Y^\ominus$ is $SO_3^\ominus$, $SO_2^\ominus$ or $COO^\ominus$ and X'' is 1,4-phenylene, 2,6-naphthylene or 4,4'-biphenylene, and also those of the formula

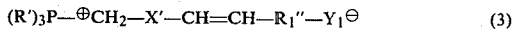  (3)

in which $R_1''$ is a phenyl or furan radical which, in addition to the group $Y_1^\ominus$, can carry one or two further substituents from the group comprising alkyl having 1 to 4 C atoms, alkoxy having 1 to 4 C atoms, cyclohexyl, alkenyl having 3 or 4 C atoms, phenyl, sulpho, fluorine, chlorine, bromine or carbalkoxy having 2 to 5 C atoms, R' is alkyl having 1 to 4 C atoms, cyclohexyl or phenyl, $Y_1^\ominus$ is $SO_3^\ominus$ or $COO^\ominus$ and X' is 1,4-phenylene or 4,4'-biphenylene.

Further compounds which are of interest are those of the formula

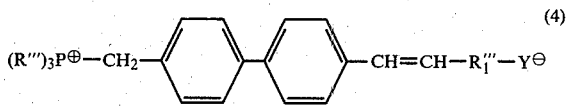  (4)

in which R''' is isopropyl, n-butyl or cyclohexyl, $R_1'''$ is a mononuclear or binuclear aromatic radical which can contain one further non-chromophoric substituent and $Y^\ominus$ is $SO_3^\ominus$, $SO_2^\ominus$ or $COO^\ominus$.

Preferred compounds are those of the formula

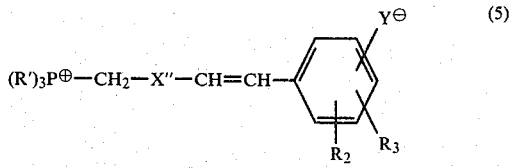  (5)

in which $Y^\ominus$ is $-SO_3^\ominus$, $-SO_2^\ominus$ or $-COO^\ominus$, $R_2$ is hydrogen, chlorine, bromine, fluorine, alkyl or alkoxy each having 1 to 4 C atoms or a further group $Y^\ominus$, $R_3$ is hydrogen, chlorine, bromine, fluorine or alkyl or alkoxy each having 1 to 4 C atoms, X'' is 1,4-phenylene, 4,4'-biphenylene or 2,6-naphthylene and R' is alkyl having 1 to 4 C atoms, cyclohexyl or phenyl, especially those of the formula

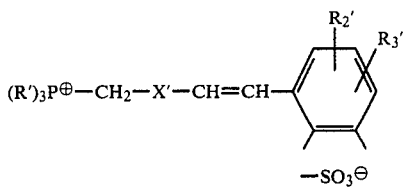

in which R' is alkyl having 1 to 4 C atoms, cyclohexyl or phenyl, $R_2'$ and $R_3'$ independently of one another are each hydrogen, chlorine, methyl, methoxy or ethoxy and X' is 1,4-phenylene or 4,4'-biphenylene, and in particular those of the formula

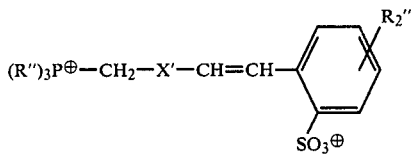

in which R" is isopropyl, n-butyl, phenyl or cyclohexyl, $R_2''$ is hydrogen or chlorine and X' is 1,4-phenylene or 4,4'-biphenylene, and of the formula

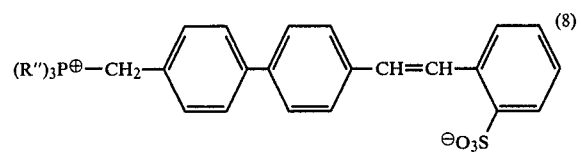

in which R" is isopropyl, n-butyl, phenyl or cyclohexyl.

The phosphonium compounds of the formulae (1) to (8) are prepared by a novel process which is also a subject of the invention.

This process for the preparation of the compounds of the formula (1) comprises reacting a phosphonium compound of the formula

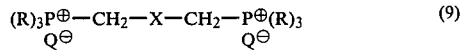

in which R and X are as defined in formula (1) and $Q^\ominus$ is an anion, in the presence of a strongly basic compound and of a polar solvent with an aldehyde of the formula $$M^\oplus Y^\ominus - R_1 - CHO \qquad (10)$$

in which $R_1$ and $Y^\ominus$ are as defined in formula (1) and $M^\oplus$ is a cation.

As mentioned, a strongly basic compound is required for the reaction. Such compounds are especially alkali metal alcoholates, in particular of sodium and potassium.

Examples of polar solvents are aprotic solvents, such as N,N-disubstituted acid amides, sulphoxides, sulphones, nitriles and N,N,N',N'-tetrasubstituted ureas, or protic solvents, for example carboxylic acids or monohydric or polyhydric primary, secondary or tertiary alcohols, preferably aliphatic monohydric primary alcohols, such as methanol or ethanol.

The basic compound/solvent system used is therefore preferably a solution of an alkali metal alcoholate in the corresponding alcohol, and this is obtained, for example, by dissolving Na or K in methanol or ethanol.

In addition to hydrogen, cations $M^\oplus$ are generally ions of alkaline earth metals, for example of Ca, Ba or Mg, and also especially of alkali metals, for example of Na or K, but also ammonium ions ($NH_4^\oplus$) or amine salt ions. Preferred amine salt ions are those which are derived from mono-, di- or tri-alkylamines, in which the alkyl radicals can also be substituted by hydroxyl, cyano or chlorine. However, the amine salt ions can also be those of cyclic amines such as pyridine, morpholine or piperidine. Preferably, $M^\oplus$ is a hydrogen, potassium, sodium or ammonium ion.

The anions $Q^\ominus$ are, in particular, anions of organic or inorganic acids, for example of formic acid, acetic acid or lactic acid or of a hydrogen halide acid, sulphuric acid or carbonic acid, and also of monoalkyl esters of sulphuric acid or an arylsulphonic acid, such as toluenesulphonic acid, benzenesulphonic acid or a halogenobenzenesulphonic acid. $Q^\ominus$ is preferably a chloride or bromide ion.

The reaction of the phosphonium compounds of the formula (9) with the aldehydes of the formula (10) is generally carried out at temperatures between 20 and 150° C., especially between 40° and 140° C. and preferably between 40° and 100° C.

The phosphonium compounds of the formulae (2) to (8) are obtained by reacting the correspondingly substituted bis-phosphonium compounds of the type indicated in formula (9) with the correspondingly substituted aldehydes of the type indicated in formula (10) by the method described above, the general symbols in each case being as defined in the formulae (2) to (8).

The bis-phosphonium compounds of the formula (9), which can be used as starting materials, are prepared in a manner known per se by reacting one mol of a dihalogen compound of the formula $$Hal - H_2C - X - CH_2 - Hal \qquad (11)$$

in which Hal is halogen, such as chlorine or bromine, and X is as defined above, with 2 mols of a phosphine of the formula $$P(R)_3 \qquad (12)$$

in which R is as defined above, [cf. A. Merker, Organic Reactions 14, 270 ff (1965) and Drefahl, Plötner and Rudolph, Chem. Ber. 93, 998 (1960)].

The starting compounds of the formula (11) are known or can easily be prepared by conventional processes, by chloromethylation of benzene, 4,4'-biphenyl or naphthalene.

The phosphines of the formula (12) are known.

The aldehydes of the formula (10) are also known or can be obtained easily by the processes described in the literature.

The phosphonium compounds, according to the invention, of the formulae (2) to (8) are valuable intermediates for the preparation of asymmetrically substituted fluorescent brightening agents of the type $$Z - CH = CH - X - CH = CH - R_1 - Y \qquad (13)$$

in which X, Y and $R_1$ are as defined in formula (1) and Z is an aromatic radical. Compounds of this type are described, for example, in U.S. Pat. Specifications 4,008,224, 3,984,399, 3,843,633 and 3,849,485. According to these Patent Specifications, asymmetrically substituted fluorescent brightening agents of this type hitherto had to be prepared by a co-condensaton reaction, in which a bis-phosphonium compound was reacted with a mixture of two different aldehydes. This method of course resulted in low yields and in not very pure products, since symmetrical compounds were always also formed as by-products.

Surprisingly, it is now possible with the aid of a novel process, in which the compounds, according to the invention, of the formula (1) are formed as intermediates and which is also a subject of the invention, to synthesise the said asymmetrically substituted fluorescent brightening agents selectively and without the formation of symmetrical by-products, and thus in good yields.

The process according to the invention for the preparation of asymmetrically substituted optical fluorescent brightening agents of the formula $$Z-CH=CH-X-CH=CH-R_1-Y^{\ominus}M^{\alpha} \quad (14)$$

in which $R_1$ is a mononuclear or binuclear aromatic carbocyclic or heterocyclic radical which can contain further non-chromophoric substituents, X is phenylene, 4,4'-biphenylene or 1,4- or 2,6-naphthylene, Z is a mononuclear or binuclear aromatic carbocyclic or heterocyclic radical which can be substituted by non-chromophoric substituents, Z differing from the group $-R_1-Y^{\ominus}M^{\oplus}$, $Y^{\ominus}$ is $SO_3^{\ominus}$, $SO_2^{\ominus}$ or $COO^{\ominus}$ and $M^{\oplus}$ is a cation, comprises reacting a phosphonium compound of the formula $$(R)_3P^{\oplus}-CH_2-X-CH_2-P^{\oplus}(R)_3 \quad (9)$$
$$Q^{\ominus} \quad\quad\quad\quad\quad\quad Q^{\ominus}$$

in which X is as defined above, R is alkyl having 1 to 6 C atoms, cycloalkyl having 5 to 7 C atoms, aryl or the group $-NX_1X_2$, in which $X_1$ and $X_2$ independently of one another are alkyl having 1 to 4 C atoms or together with the N atom are a 5-membered or 6-membered saturated heterocyclic ring, and $Q^{\ominus}$ is an anion, in the presence of a strongly basic compound in a polar solvent with an aldehyde of the formula $$M^{\oplus}Y^{\ominus}-R_1-CHO \quad (10)$$

in which $R_1$, $Y^{\ominus}$ and $M^{\oplus}$ are as defined above, at temperatures between 20 and 150° C. and reacting the resulting reaction product of the formula $$(R)_3P^{\oplus}-CH_2-X-CH=CH-R_1-Y^{\ominus} \quad (1)$$

after this has been isolated or directly in the reaction mixture, with an aldehyde of the formula Z-CHO at temperatures of 100° to 200° C. in the presence of a strongly basic compound in a polar solvent which boils above 100° C.

The general symbols in formula (14) are defined in more detail in the definitions given above for the formulae (1), (9) and (10). The substituent Z can preferably have the meanings defined for $R_1$ and can contain the same substituents (see above) but in the molecule is not identical to the latter.

The process parameters for the first stage correspond to those for the process for the preparation of the compounds of the formula (1). The explanations given for that process therefore also apply here.

The intermediate of the formula (1) can be isolated but can also be reacted further direct in the reaction mixture, without isolation, with the aldehyde Z-CHO, if appropriate after evaporating off the solvent. Preferably, however, the intermediate is isolated.

A strongly basic compound is also required for the second stage, i.e. the reaction of the intermediate of the formula (1) with the aldehyde Z—CHO. Strongly basic compounds for this stage are alkali metal hydroxides and alkaline earth metal hydroxides, for example KOH or NaOH, and also alkali metal alcoholates or metallic sodium or potassium in corresponding solvents.

The polar solvents are those with a boiling point of above 100° C., for example aprotic solvents, such as N,N-disubstituted acid amides, sulphoxides, sulphones, nitriles and N,N,N',N'-tetrasubstituted ureas, or protic solvents, for example carboxylic acids or higher-boiling alcohols, for example tertiary and especially secondary alchols. Ethylene glycol is a preferred solvent.

The process according to the invention is preferably used to prepare compounds of the formulae

  (15) and

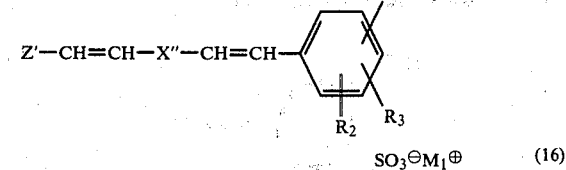  (16)

in which $M_1^{\oplus}$ is a hydrogen, alkali metal, alkaline earth metal, ammonium or amine ion, $Y^{\ominus}$ is $-SO_3^{\ominus}$, $-SO_2^{\ominus}$ or $-COO^{\ominus}$, $R_2$ is hydrogen, chlorine, bromine, fluorine, alkyl or alkoxy each having 1 to 4 C atoms or the group $Y^{\ominus}M_1^{\oplus}$, $R_3$ is hydrogen, chlorine, bromine, fluorine or alkyl or alkoxy each having 1 to 4 C. atoms, X" is 1,4-phenylene, 4,4'-biphenylene or 2,6-naphthylene, Z' is a group of the formula

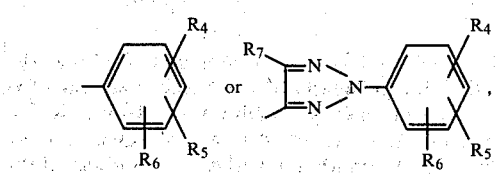

in which $R_4$ is hydrogen, chlorine, bromine, fluorine, alkyl or alkoxy each having 1 to 4 C. atoms or cyano or together with $R_5$ in the ortho-position is the radical $-O-CH_2-O-$ or $-O-CH_2-O-CH_2-$, $R_5$ is hydrogen, chlorine, bromine, fluorine or alkyl or alkoxy each having 1 to 4 C. atoms or together with $R_4$ in the ortho-position is the radical $-O-CH_2-O-$ or $-O-CH_2-O-CH_2-$, $R_6$ is hydrogen, chlorine, bromine, fluorine or alkyl having 1 to 4 C. atoms and $R_7$ is hydrogen, alkyl having 1 to 4 C. atoms, chlorine or phenyl, X' is 1,4-phenylene or 4,4'-biphenylene and Z" is a group of the formula

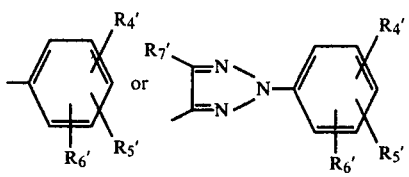

in which R$_4$' is hydrogen, chlorine, methyl, methoxy or ethoxy or together with R$_5$' in the ortho-position is the radical —O—CH$_2$—O— or —O—CH$_2$—O—CH$_2$—, R$_5$' is hydrogen, chlorine, methyl, methoxy or ethoxy or together with R$_4$' in the ortho-position is the radical —O—CH$_2$—O— or —O—CH$_2$—O—CH$_2$—, R$_6$' is hydrogen, chlorine or methyl and R$_7$' is hydrogen, methyl or ethyl, by reacting a bisphosphonium compound of the formula

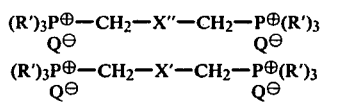

with an aldehyde of the formula

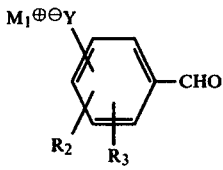

and reacting the resulting intermediate with an aldehyde of the formula Z'—CHO or Z"—CHO respectively.

It is preferred to prepare compounds of the formula

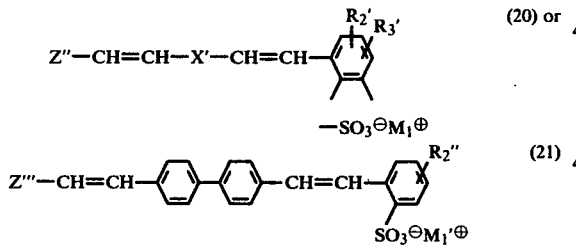

in which X', Z" and M$_1$⊕ are as defined in formula (16), R$_2$' and R$_3$' independently of one another are each hydrogen, chlorine, methyl, methoxy or ethoxy, R$_2$" is hydrogen or chlorine, M$_1$'⊕ is a hydrogen, sodium, potassium or ammonium ion and Z'" is a radical of the formula

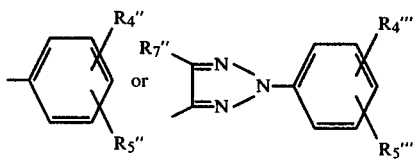

in which R$_4$" is hydrogen, chlorine, methyl or methoxy or together with R$_5$" in the ortho-position is the group of the formula —O—CH$_2$—O—CH$_2$—, R$_5$" is hydrogen, chlorine or methyl or together with R$_4$" in the ortho-position is the group of the formula —O—CH- $_2$—O—CH$_2$—, R$_4$'" is hydrogen, chlorine, methyl, methoxy or ethoxy, R$_5$'" is hydrogen, chlorine or methyl and R$_7$" is hydrogen or methyl, by reacting a bis-phosphonium compound of the formula

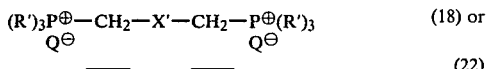

with an aldehyde of the formula

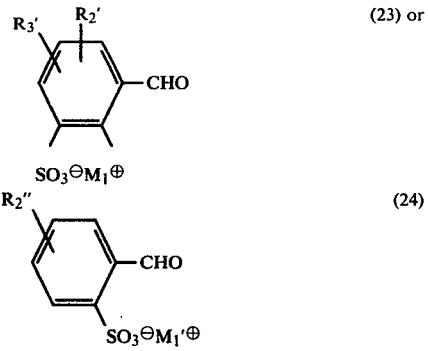

respectively and reacting the resulting intermediate with an aldehyde of the formula Z"—CHO or Z'"—CHO respectively.

If, in formula (22), the biphenylene radical is replaced by a phenylene radical, this results in fluorescent brightening agents of the formula (21) which contain a phenylene radical in place of the biphenylene radical and which are also preferred.

The following examples illustrate the invention without restricting it to these examples. Percentages and parts are by weight unless stated otherwise.

EXAMPLE 1

0.253 g of metallic sodium is dissolved in portions in 50 ml of anhydrous methanol, with stirring, in a nitrogen atmosphere, in a 200 ml flask. 6.56 g of the phosphonium compound of the formula

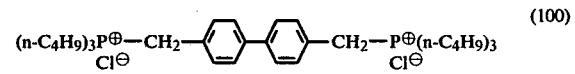

and 2.53 g of the sodium salt of benzaldehyde-2-sulphonic acid (91% pure) are then added to the alcoholate solution. The reaction mixture is warmed to 40° to 45° C. and stirred for 16 hours. 80 ml of water are added to the resulting white suspension and the mixture is stirred for 1 hour at the boil. The white suspension is now filtered with suction and the material on the filter is washed with a large amount of boiling water and dried in vacuo at 100° C. for 24 hours. This yields 5.48 g (98% of theory) of the compound of the formula

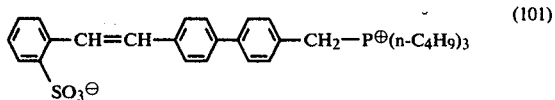

which has a $\lambda_{max}$ of 335 nm in dimethylformamide.

Analysis: Calculated: C 71.97; H 7.87; S 5.82; P 5.62; Found: C 71.3; H 7.6; S 5.9; P 5.6.

If the compounds of the formulae

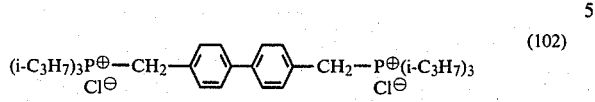

(102)

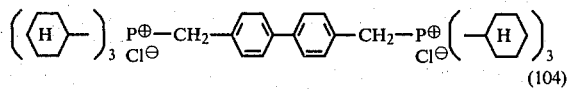

(103) and (104)

are used in place of the compound of the formula (100) and in other respects the procedure is as described in Example 1, the compounds of the following formulae are obtained:

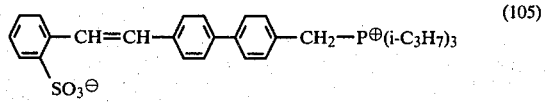

(105)

Yield: 40%
$\lambda_{max}$ = 330 nm in dimethylformamide

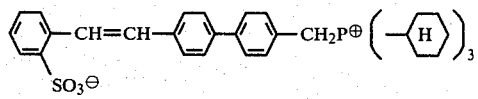

(106)

Yield: 80%
$\lambda_{max}$ = 320 nm in dimethylformamide/water, and

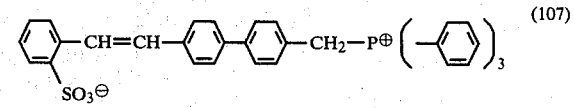

(107)

Yield: 90%
$\lambda_{max}$ = 329 nm in ethanol.

When compound (104) is used, the reaction with the sodium salt of benzaldehyde-2-sulphonic acid is carried out in the presence of molar amounts of sodium bisulphite in order to prevent the formation of a 1:1 cis/trans mixture. The compound of the formula (104) can, for example, also be reacted with the sodium salt of 2-formyl-furan-5-sulphonic acid in accordance with the method described in Example 1, in which case the compound of the formula

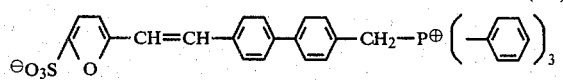

(108)

is obtained.
Yield: 90%
$\lambda_{max}$ = 350 nm in methylene chloride.

EXAMPLE 2

The process according to Example 1 is repeated except that compound (100) is replaced by the corresponding bis-phosphonomethyl-benzene, -biphenyl and -naphthalene compounds have benzaldehyde-2-sulphonic acid is replaced by 5-sulpho-furfurol, affording the compounds of the formula

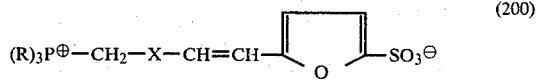

(200)

listed in Table 1.

TABLE 1

| Compound No. | R | X | Yield |
|---|---|---|---|
| 201 | n-C$_4$H$_9$ | 4,4'-biphenylene | 93.4 |
| 202 | n-C$_4$H$_9$ | 1,4-phenylene | 88.3 |
| 203 | phenyl | 1,4-phenylene | 91.9 |

EXAMPLE 3

The process according to Example 1 is repeated except that compound (100) is replaced by the corresponding bis-phosphonomethyl-benzene, -biphenyl and -naphthalene compounds and the latter are reacted with correspondingly substituted benzaldehydes, affording the compounds of the formula

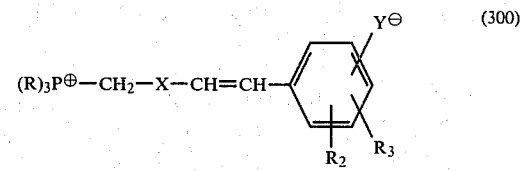

(300)

listed in Table 2.

TABLE 2

| Compound No. | R | X | R$_2$ | R$_3$ | Y$^\ominus$ |
|---|---|---|---|---|---|
| 204 | n-C$_4$H$_9$ | 1,4-phenylene | H | H | 2-SO$_3^\ominus$ |
| 205 | phenyl | 1,4-phenylene | H | H | 2-SO$_3^\ominus$ |
| 206 | cyclohexyl | 1,4-phenylene | H | H | 2-SO$_3^\ominus$ |
| 207 | n-C$_4$H$_9$ | 4,4'-biphenylene | H | H | 2-COO$^\ominus$ |
| 208 | N-C$_4$H$_9$ | 4,4'-biphenylene | H | H | 4-COO$^\ominus$ |
| 209 | n-C$_4$H$_9$ | 4,4'-biphenylene | 4-Cl | H | 3-SO$_3^\ominus$ |
| 210 | cyclohexyl | 4,4'-biphenylene | H | H | 4-SO$_2^\ominus$ |
| 211 | i-C$_3$H$_7$ | 4,4'-biphenylene | 3-Cl | H | 2-SO$_3^\ominus$ |
| 212 | N-C$_4$H$_9$ | 4,4'-biphenylene | 4-Cl | H | 2-SO$_3^\ominus$ |
| 213 | phenyl | 4,4'-biphenylene | 2-SO$_3$H | H | 4-SO$_3^\ominus$ |
| 214 | cyclohexyl | 4,4'-biphenylene | 3-CH$_3$ | 4-CH$_3$ | 2-SO$_3^\ominus$ |
| 215 | n-C$_4$H$_9$ | 4,4'-biphenylene | 4-OCH$_3$ | H | 2-SO$_3^\ominus$ |
| 216 | CH$_3$ | 4,4'-biphenylene | H | H | 2-COO$^\ominus$ |
| 217 | phenyl | 4,4'-biphenylene | 3-Cl | 4-CH$_3$ | 2-SO$_3^\ominus$ |
| 218 | n-C$_4$H$_9$ | 4,4'-biphenylene | 2-Cl | H | 3-SO$_3^\ominus$ |
| 219 | N-C$_4$H$_9$ | 4,4'-biphenylene | 2-CH$_3$ | H | 3-SO$_3^\ominus$ |
| 220 | n-C$_4$H$_9$ | 1,4-phenylene | 3-CH$_3$ | H | 4-COO$^\ominus$ |
| 221 | n-C$_4$H$_9$ | 1,4-naphthylene | H | H | 2-SO$_3^\ominus$ |
| 222 | n-C$_4$H$_9$ | 2,6-naphthylene | H | H | 2-SO$_3^\ominus$ |

EXAMPLE 4

5.5 ml of 2N NaOH in ethylene glycol and 45 ml of ethylene glycol are initially introduced, under a nitrogen atmosphere, into a 200 ml flask. 5.58 g of compound (101) and 2.22 g of the bisulphite adduct of the aldehyde of the formula M=Na, K or H listed in Table 3.

TABLE 3

| Compound No. | R$_3$ | R$_4$ | R$_7$ | R$_2$ | R$_3$ | Y$^\ominus$ |
|---|---|---|---|---|---|---|
| 403 | H | H | CH$_3$ | H | H | 2-SO$_3^\ominus$ |
| 404 | 3-Cl | H | H | H | H | 2-SO$_3^\ominus$ |
| 405 | 4-CH$_3$ | H | H | H | H | 2-SO$_3^\ominus$ |
| 406 | H | H | H | 3-Cl | H | 2-SO$_3^\ominus$ |
| 407 | H | H | H | 4-Cl | H | 2-SO$_3^\ominus$ |
| 408 | 3-CH$_3$ | H | H | H | H | 2-SO$_3^\ominus$ |
| 409 | 3-OCH$_3$ | H | H | H | H | 2-SO$_3^\ominus$ |
| 410 | 3-F | H | H | H | H | 2-SO$_3^\ominus$ |
| 411 | 4-F | H | H | H | H | 2-SO$_3^\ominus$ |
| 412 | 4-Cl | H | H | H | H | 2-SO$_3^\ominus$ |
| 413 | 3-CH$_3$ | 4-Cl | H | H | H | 2-SO$_3^\ominus$ |
| 414 | 3-Br | H | H | H | H | 2-SO$_3^\ominus$ |
| 415 | 3-Br | 4-Br | H | H | H | 2-SO$_3^\ominus$ |
| 416 | 2-CH$_3$ | 4-Br | H | H | H | 2-SO$_3^\ominus$ |
| 417 | 4-C$_2$H$_5$ | H | H | H | H | 2-SO$_3^\ominus$ |
| 418 | 3-CH$_3$ | 4-CH$_3$ | H | H | H | 2-SO$_3^\ominus$ |
| 419 | 3,4-O—CH$_2$—O—CH$_2$— | | H | H | H | 4-SO$_3^\ominus$ |
| 420 | 3,4-O—CH$_2$—O— | | H | H | H | 3-SO$_3^\ominus$ |
| 421 | H | H | C$_6$H$_5$ | H | H | 2-SO$_3^\ominus$ |
| 422 | H | H | H | 2-SO$_3$Na | H | 4-SO$_3^\ominus$ |
| 423 | H | H | H | 3-CH$_3$ | 4-CH$_3$ | 2-SO$_3^\ominus$ |
| 424 | H | H | H | 4-OCH$_3$ | H | 2-SO$_3^\ominus$ |
| 425 | H | H | H | H | H | 4-COO$^\ominus$ |
| 426 | 3-Cl | H | H | 3-Cl | 4-CH$_3$ | 2-SO$_3^\ominus$ |

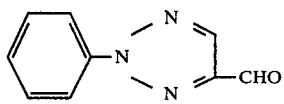

(400)

are added to this solution. The resulting white suspension is warmed to 140° C. and stirred for 4 hours. The ethylene glycol is distilled off in vacuo, 100 ml of a water/dimethylformamide mixture (9:1) are added to the residue and the whole is heated to the boil. The hot solution is filtered with the aid of bleaching earth and the material on the filter is washed with 50 ml of water/dimethylformamide (9:1). The filtrate is heated to the boil until everything has dissolved. 14 g of NaCl are then added and the mixture is allowed to cool. The green-yellow product formed is filtered off with suction, washed with 15 ml of 10% strength NaCl solution and dried for 24 hours in vacuo at 100° C. This yields 4.53 g (86% of theory) of the fluorescent brightening agent of the formula

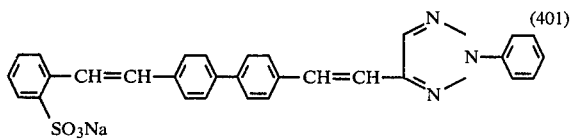

(401)

The above method of preparation is repeated except that compound (101) is replaced by the corresponding compound described in Example 1 or 3 and the aldehyde (400) is replaced by a correspondingly substituted aldehyde, affording the compounds of the formula

EXAMPLE 5

0.25 g (0.01 mol) of sodium is dissolved in 100 ml of ethylene glycol at 40° to 45° C. and 5.5 g (0.01 mol) of the compound of the formula (101) and 1.16 g (0.011 mol) of benzaldehyde are then added to the clear solution under a nitrogen atmosphere, with stirring. The mixture is warmed to 140° C. and stirred overnight, during which time a yellow-green suspension forms. The reaction mixture is then cooled to about 80° C. and the solvent is distilled off under a waterpump vacuum. The residue is digested three times in 50 ml of toluene and boiled in order to remove residues of aldehyde and tri-butylphosphine oxide. The residue, which is now solid, is boiled up in 100 ml of 9:1 water/dimethylformamide, the boiling solution is filtered, the filtrate is again brought to the boil and 10 g of NaCl are added. The yellowish suspension is allowed to cool, with stirring, and is stirred for about a further 3 hours at room temperature and the product is filtered off, washed with a little 10% NaCl solution and dried at 120° C. in vacuo. About 4 g of the fluorescent brightening agent of the formula

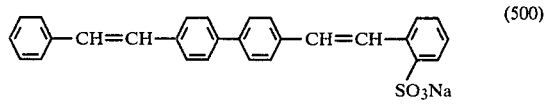

(500)

are thus obtained.

The compounds of the formula

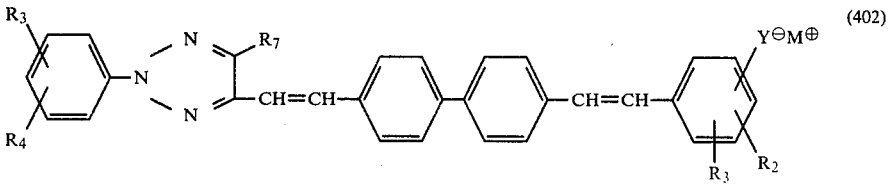

(402)

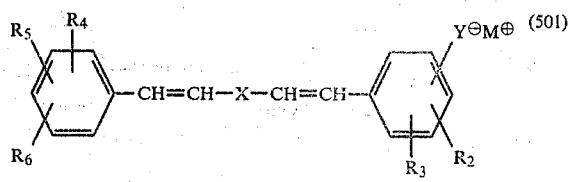

M = Na, K or H listed in Table 4 are obtained in an analogous manner using the corresponding phosphonium compounds obtained according to Examples 1 and 3 and the correspondingly substituted aldehydes.

TABLE 4

| Compound No. | $R_4$ | $R_5$ | $R_6$ | X | $R_2$ | $R_3$ | $Y^\ominus$ |
|---|---|---|---|---|---|---|---|
| 502 | 2-$CH_3$ | H | H | 4,4'-Biphenylene | H | H | 2-$SO_3^\ominus$ |
| 503 | 2-Cl | H | H | 4,4'-Biphenylene | H | H | 2-$SO_3^\ominus$ |
| 504 | 4-$OCH_3$ | H | H | 4,4'-Biphenylene | H | H | 2-$SO_3^\ominus$ |
| 505 | 3-Cl | H | H | 4,4'-Biphenylene | H | H | 2-$SO_3^\ominus$ |
| 506 | 4-$CH_3$ | H | H | 4,4'-Biphenylene | H | H | 2-$SO_3^\ominus$ |
| 507 | 3,4-O—$CH_2$—O—$CH_2$— | H | H | 4,4'-Biphenylene | H | H | 2-$SO_3^\ominus$ |
| 508 | 3,4-O—$CH_2$—O— | | H | 4,4'-Biphenylene | H | H | 2-$SO_3^\ominus$ |
| 509 | 3-CN | H | H | 4,4'-Biphenylene | H | H | 2-$SO_3^\ominus$ |
| 510 | 2-Cl | 4-Cl | H | 4,4'-Biphenylene | H | H | 2-$SO_3^\ominus$ |
| 511 | 2-$OCH_3$ | H | H | 4,4'-Biphenylene | H | H | 2-$SO_3^\ominus$ |
| 512 | 2-Cl | 6-Cl | H | 4,4'-Biphenylene | H | H | 2-$SO_3^\ominus$ |
| 513 | 2-$CH_3$ | 4-$CH_3$ | 6-Cl | 4,4'-Biphenylene | H | H | 2-$SO_3^\ominus$ |
| 514 | 2-$OCH_3$ | 3-$OCH_3$ | H | 4,4'-Biphenylene | H | H | 2-$SO_3^\ominus$ |
| 515 | 3-F | H | H | 4,4'-Biphenylene | H | H | 2-$SO_3^\ominus$ |
| 516 | 4-t-$C_4H_9$ | H | H | 4,4'-Biphenylene | H | H | 2-$SO_3^\ominus$ |
| 517 | 3-Cl | 4-$CH_3$ | H | 4,4'-Biphenylene | H | H | 2-$SO_3^\ominus$ |
| 518 | 2-$C_2H_5$ | 4-$C_2H_5$ | H | 4,4'-Biphenylene | H | H | 2-$SO_3^\ominus$ |
| 519 | H | H | H | 4,4'-Biphenylene | 2-Cl | H | 3-$SO_3^\ominus$ |
| 520 | 2-Cl | H | H | 4,4'-Biphenylene | 2-$CH_3$ | H | 3-$SO_3^\ominus$ |
| 521 | 3-$OCH_3$ | H | H | 4,4'-Biphenylene | 4-Cl | H | 3-$SO_3^\ominus$ |
| 522 | H | H | H | 4,4'-Biphenylene | 3-Cl | 4-$CH_3$ | 2-$SO_3^\ominus$ |
| 523 | H | H | H | 4,4'-Biphenylene | H | H | 2-$SO_2^\ominus$ |
| 524 | H | H | H | 4,4'-Biphenylene | 3-$CH_3$ | H | 4-$COO^\ominus$ |
| 525 | 2-$OCH_3$ | H | H | 1,4-Phenylene | H | H | 2-$SO_3^\ominus$ |
| 526 | 2-$OCH_3$ | 3-$OCH_3$ | H | 1,4-Phenylene | H | H | 2-$SO_3^\ominus$ |
| 527 | 4-Cl | H | H | 1,4-Phenylene | H | H | 2-$SO_3^\ominus$ |
| 528 | 2-Cl | 4-Cl | H | 1,4-Phenylene | H | H | 2-$SO_3^\ominus$ |
| 529 | 2-$CH_3$ | H | H | 1,4-Phenylene | H | H | 2-$SO_3^\ominus$ |
| 530 | 3-Cl | H | H | 1,4-Phenylene | 2-$SO_3Na$ | H | 4-$SO_3^\ominus$ |
| 531 | H | H | H | 1,4-Naphthylene | H | H | 2-$SO_3^\ominus$ |
| 532 | H | H | H | 2,6-Naphthylene | H | H | 2-$SO_3^\ominus$ | in which R'' is isopropyl, n-butyl, phenyl or cyclohexyl, $R_2''$ is hydrogen or chlorine and X' is 1,4-phenylene or 4,4'-biphenylene.

3. The phosphonium compound according to claim 2 of the formula

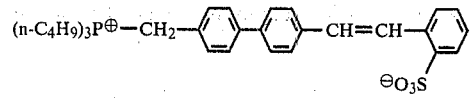

4. A phosphonium compound according to claim 1, of the formula

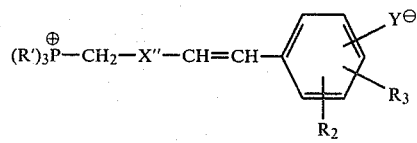

in which $Y^\ominus$ is —$SO_3^\ominus$, $R_2$ is hydrogen, chlorine, bromine, fluorine, alkyl or alkoxy each having 1 to 4 C atoms or a further group $Y^\ominus$, $R_3$ is hydrogen, chlorine, bromine, fluorine or alkyl or alkoxy each having 1 to 4 C atoms, X'' is 1,4-phenylene, 4,4'-biphenylene or 2,6-naphthylene and R' is alkyl having 1 to 4 C atoms, cyclohexyl or phenyl.

5. A phosphonium compound according to claim 1, of the formula

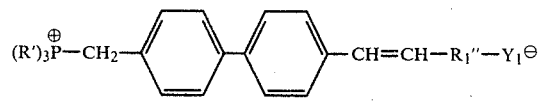

What is claimed is:
1. A phosphonium compound of the formula
$(R')_3P$—$^\oplus CH_2$—X'—CH=CH—$R_1''$—$Y_1^\oplus$ in which $R_1''$ is a phenyl radical which, in addition to the group $Y_1^\ominus$, can carry one or two further substituents from the group comprising alkyl having 1 to 4 C atoms, alkoxy having 1 to 4 C atoms, cyclohexyl, alkenyl having 3 or 4 C atoms, phenyl, sulpho, fluorine, chlorine, bromine or carbalkoxy having 2 to 5 C atoms, R' is alkyl having 1 to 4 C atoms, cycloalkyl having 5-7 C atoms or phenyl, $Y_1^\ominus$ is $SO_3^\ominus$ and X' is 1,4-phenylene, 4,4'-biphenylene or 1,4- or 2,6-naphthylene.

2. A phosphonium compound according to claim 1, of the formula

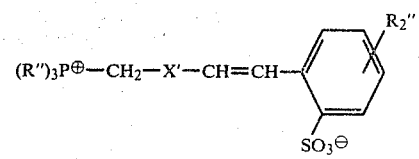

in which R' is isopropyl, n-butyl or cyclohexyl, $R_1''$ is as defined in claim 3 and $Y_1^\ominus$ is $SO_3^\ominus$.
6. A phosphonium compound according to claim 4, of the formula
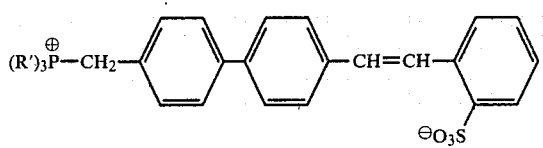
in which R' is isopropyl, n-butyl, phenyl or cyclohexyl.
* * * * *

UNITED STATES PATENT AND TRADEMARK OFFICE
CERTIFICATE OF CORRECTION

PATENT NO. : 4,231,957
DATED : November 4, 1980
INVENTOR(S) : Michael Marky

It is certified that error appears in the above-identified patent and that said Letters Patent are hereby corrected as shown below:

Claim 1, Column 13, Line 48 reads:

"$(r')_3P-^{\oplus}CH_2-X'-CH=CH-R_1''-Y_1^{\oplus}$".

Should read:

"$(R')_3P-^{\oplus}CH_2-X'-CH=CH-R_1''-Y_1^{\ominus}$".

Signed and Sealed this

Seventh Day of April 1981

[SEAL]

Attest:

RENE D. TEGTMEYER

Attesting Officer     Acting Commissioner of Patents and Trademarks